US00PP08256P

United States Patent [19]

Danziger

[11] Patent Number: Plant 8,256

[45] Date of Patent: Jun. 15, 1993

[54] SOLIDASTER PLANT NAMED GOLDENTOP

[75] Inventor: Michael Danziger, Mishmar Hashiva, Israel

[73] Assignee: Danziger—"Dan" Flower Farm, Mishmar Hashiva, Israel

[21] Appl. No.: 755,513

[22] Filed: Aug. 26, 1991

[51] Int. Cl.[5] ..... A01H 5/00
[52] U.S. Cl. ..... Plt.68.1
[58] Field of Search ..... Plt./68.1

[56] References Cited

PUBLICATIONS

Huxley, A., et al., (Eds.) "Solidmaster" *Dictionary of Gardening 4*, 1992 The Stockton Press, N.Y. p. 326.

*Primary Examiner*—James R. Feyrer
*Attorney, Agent, or Firm*—Foley & Lardner

[57] ABSTRACT

A new and distinct cultivar of solidaster named Goldentop, characterized by its intense relatively dark yellow flowers, relatively small diameter flowers, narrow leaves, dark green leaf color, and its floriferous habit.

1 Drawing Sheet

The present invention comprises a new and distinct cultivar of solidaster plant hereinafter referred to by the cultivar name Goldentop.

Solidaster is a hybrid genus resulting from the crossing of *Aster ptarmicoides* with an unknown species of goldenrod of the genus Solidago. The single species of solidaster, *S. luteus* (sometimes referred to as *Aster hybridus luteus*), is a perennial herb approximately 45 to 65 cm in height, with narrow leaves and small daisy-type flowers carried on numerous clusters of branches. Cultivation is similar to the perennial species of the genus Aster.

Goldentop is a natural mutation discovered by applicant in July 1988 in Mishmar Hashiva, Israel in a cultivated area. The new cultivar was discovered and selected while growing among plants of an unnamed parent cultivar of solidaster. The new cultivar was recognized and selected due to its darker yellow flower color, smaller flowers, and narrower and darker green leaves, when compared to the parent cultivar.

The new cultivar was first asexually reproduced by applicant by leaf and stem cuttings taken at Mishmar Hashiva, Israel. Such asexual reproduction has demonstrated that the combination of characteristics as herein disclosed for the new cultivar are firmly fixed and retained through successive generations of asexual reproduction.

Goldentop has not been observed under all possible environmental conditions. The following observations, measurements and values describe the new cultivar as grown in Mishmar Hashiva, Israel under conditions which closely approximate those generally used in commercial practice.

The following traits have been repeatedly observed and are determined to be basic characteristics of Goldentop, which, in combination, distinguish the solidaster as a new and distinct cultivar:

1. The flower color of Goldentop is darker yellow than the parent cultivar.
2. The size of the flowers of Goldentop is smaller than the flowers of the parent cultivar.
3. The leaves of Goldentop are shorter and narrower than the parent cultivar, and the color of the leaves is a darker green than the parent.

The new cultivar is generally similar to the parent cultivar in growth habit, overall height and floriferousness. Goldentop differs from its parent in the noted respects. The flower color of Goldentop is a much darker yellow than the color (R.H.S. 3B) of the parent, its flowers are smaller in diameter (0.8 cm vs. 1.2 cm), its leaves are shorter (approximately 12 cm vs. 14 cm) and narrower (2 cm vs. 3 cm) than the parent, and its leaves are darker green in color (R.H.S. 137A vs. 137C).

The accompanying color photographic drawings illustrate a typical specimen plant of the new cultivar. The colors appearing in the photographs are as true as possible with color illustrations of this type.

The top photograph is a top perspective view of a large portion of a typical plant.

The photograph at the bottom is an enlarged view of a smaller group of flower clusters.

In the following description, color references are made to The Royal Horticultural Society Colour Chart (R.H.S.), except where general colors of ordinary significance are referred to. Color values were taken under artificial light at approximately noon in Mishmar Hashiva.

Botanical classification: *Solidaster luteus* cv. Goldentop.

Parentage: Natural occurring mutation of unnamed solidaster cultivar.

Propagation: The new cultivar holds its distinguishing characteristics through successive propagations by leaf and stem cuttings. The cultivar is sterile and cannot be propagated by seed.

INFLORESCENCE

A. Capitulum:
- *Form.*—Round.
- *Type.*—Daisy, with two rows of petals.
- *Diameter across face.*—Approximately 0.8 cm.

B. Corolla of ray florets:
- *Color (general tonality from a distance of three meters).*—Yellow.
- *Color (upper surface).*—13B.
- *Color (under surface).*—13B.
- *Shape.*—Round.

C. Corolla of disc florets:
- *Color (mature).*—15A.
- *Color (immature).*—15A.
- *Diameter of disc.*—0.3 cm D. Flowers borne: Each branch contains many buds which, when the buds open, produce a prolific display of flowers.

E. Reproductive organs:

*Androecium.*—Present on disc florets; pollen 15B.

*Gynoecium.*—Present on ray and disc florets, typical for the species; 3B in color.

PLANT

A. General appearance: Perennial plant with 7 to 10 stems after pinching. The height of the branches are 70 to 100 cm. The main branch has many side branches.

B. Foliage:

*Color.*—137A.

*Shape.*—Relatively long, elliptical.

*Size.*—Approximately 12 cm long and 2 cm wide at the widest point.

I claim:

1. A new and distinct cultivar of solidaster plant named Goldentop, as illustrated and described.

* * * * *

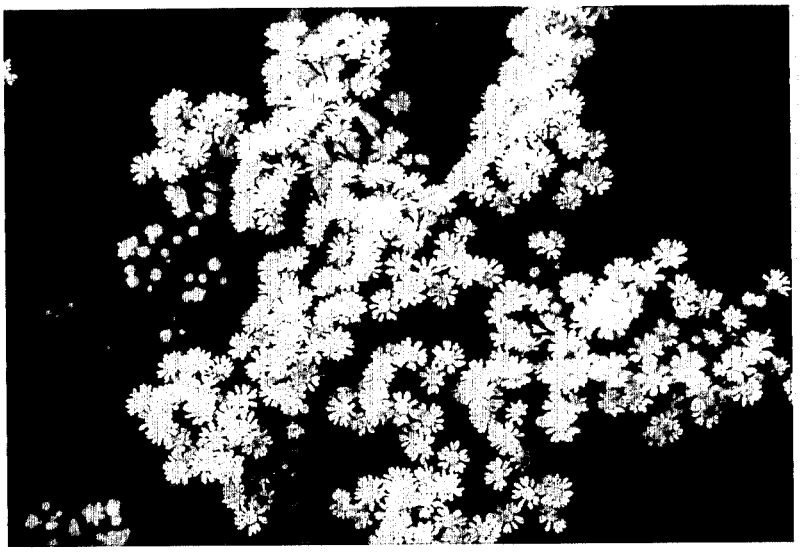
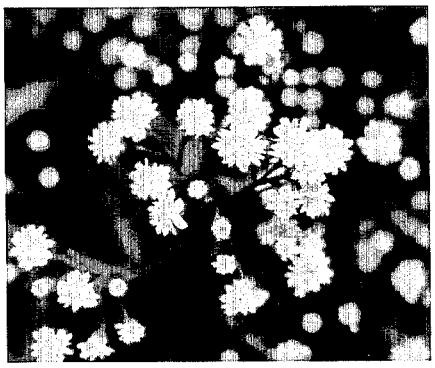
Golden Top